United States Patent [19]

Carlson et al.

[11] Patent Number: 5,213,795
[45] Date of Patent: May 25, 1993

[54] ENCEPHALOMYOCARDITIS VIRUS VACCINE

[75] Inventors: Jack H. Carlson, Worthington; Han S. Joo, New Brighton, both of Minn.

[73] Assignee: Oxford, Worthington, Minn.

[21] Appl. No.: 602,967

[22] Filed: Oct. 24, 1990

[51] Int. Cl.$^5$ .......................... A61K 39/12; C12N 7/00
[52] U.S. Cl. ....................................... 424/89; 424/88; 435/235.1; 435/236; 435/238
[58] Field of Search ................. 424/89, 88; 435/235.1, 435/236, 238

[56] References Cited

PUBLICATIONS

Bogaerts et al., *Infection and Immunity*, vol. 6, pp. 508–512, 1972.
Acland et al., *The Iowa State University Press*, Dunne et al., Ed. pp. 339–343, 1981.
Matsumori et al., *Biological Abstracts*, vol. 85, (5), Ref. No. 48849, 1987.
Kim et al., *Arch. Virol.* vol. 109, pp. 51–57, 1989.
Boulton, J., (1987), Can. Vet. J., 28:713.
Littlejohns, I., Aust. Vetern. J. 61:93 (1984).
Norkiss, A., et al. (1982), New Eng. J. Med. 306:486.
Successful Farming (1989) 87:112.
National Hog Farmer (Nov. 1989).

*Primary Examiner*—Michael G. Wityshyn
*Assistant Examiner*—Abdel A. Mohamed
*Attorney, Agent, or Firm*—Debbie K. Wright; Thomas A. Wootton

[57] ABSTRACT

The present invention provides an inactivated encephalomyocarditis virus (EMCV) vaccine produced from swine isolates which protects swine from diseases caused by EMCV. The vaccine is produced from swine isolates and protects against respiratory problems, myocardial and pulmonary inflammation and necrosis, and confers protection against reproductive disorders resulting from some strains of the virus.

4 Cla

ENCEPHALOMYOCARDITIS VIRUS VACCINE

FIELD OF THE INVENTION

This invention relates to an inactivated vaccine which protects vaccinates from clinical disease caused by encephalomyocarditis virus.

BACKGROUND OF THE INVENTION

Encephalomyocarditis virus (EMCV) is a cardiovirus within the Picornaviridae family. EMCV behaves as an enterovirus in rats, the most common carriers of the virus, as EMCV persists in the gut of these animals for extended periods of time. (Acland, H. and Littlejohns, I.; "Encephalomyocarditis", Diseases of Swine, editors, Leman, A., et al, The Iowa State University Press, 1981, page 339-343). The host range is very broad and includes primates, mice, elephants, squirrels and swine.

Populations of swine, particularly young pigs, are extremely susceptible to EMCV. The virus causes a variety of disease syndromes, including reproductive losses resulting from stillborn, mummified or weak pigs at farrowing. (Links, I., et a., (1986) Aust. Vetern. J. 63:150–151). When suckling or young feeder pigs are infected by the virus, mortality may occur as the result of clinical encephalitis, myocarditis or pneumonia. (Link, supra, and Littlejohn, I., (1984) Aust. Vetern. J. 61:93). Clinically ill pigs that do not die become inefficient feeders, resulting in performance losses in fattening pigs.

Currently, there is no known treatment for an EMCV infection in swine and prevention appears to be limited to the control of rodents on pig farms. (See Acland, supra). The instant invention provides a more effective and efficient means of preventing an EMCV infection in pigs.

INFORMATION DISCLOSURE STATEMENT

Antibodies to EMCV have been found in pigs, Boulton, J., (1987), Can. Vet. J., 28:713, and the virus has been isolated from partially mummified stillborn pigs. Littlejohns, I., Aust. Vetern. J. 61:93 (1984). A live-attenuated EMCV vaccine has been shown to prevent virus-induced diabetes in mice. Norkiss, A., et al (1982), New Eng. J. Med. 306:486. Bogaerts, W. and Durville-Van der Oond, B., (1972) Infection and Immunity 6:508–512, discloses a purified and inactivated EMCV vaccine suitable for immunization of mice. Prior to the instant invention, no comparable EMCV vaccine for pigs has been developed. See e.g., Acland H. and Littlejohn, I., "Encephalomyocarditis", Diseases of Swine, 1981, The Iowa State University Press, Dunne, H., et al., Ed. Pg. 339-343.

It has also been disclosed that an experimental EMCV vaccine aids in reducing clinical signs of a disease caused by EMCV. Successful farming (1989) 87:112. However, that publication is after the present invention was made and less than one year prior to the date of this application. The National Hog Farmer (1989), disclosed in November that EMC has been diagnosed across the United States and that researchers have shown a positive effect from vaccination. That publication was also made after the present invention and is less than one year prior to the date of this application.

SUMMARY OF THE INVENTION

The present invention relates to a vaccine which protects swine from clinical disease caused by EMCV comprising inactivated encephalomyocarditis virus-25, adjuvant and a veterinary pharmaceutically acceptable carrier. More particularly, the present invention relates to a vaccine comprising inactivated EMCV-25 having a pre-inactivation titer of about $5 \times 10^6 - 1 \times 10^9 TCID_{50}$/dose. The present invention also relates to a method of protecting swine against virulent EMC virus which comprises parenterally inoculating the animal with an inactivated EMCV vaccine. The EMC-25 strain is on deposit with the American Type Culture Collection in Rockville, Md. The deposit number is ATCC VR-2290. The deposit date is Nov. 6, 1990.

By "inactivated" we mean that the infectively of EMCV-25 has been destroyed by physical or chemical means.

By "passage" we mean the transfer of cells from one flask to another.

By "master seed" we mean a lot of the EMCV-25 which has been selected and permanently stored from which all other seed passages are derived.

By "production seed" we mean the EMCV-25 which is used without further propagation for initiating the preparation of a vaccine.

DETAILED DESCRIPTION OF THE INVENTION

The present invention relates to a killed vaccine which protects vaccinates, e.g., swine from clinical disease caused by EMCV. The vaccine also produces a high antibody titer. EMC-25 strain of EMCV is used for manufacturing an inactivated EMCV vaccine.

The vaccine comprises a sufficient amount of the EMCV antigen to produce an immunological response in swine and a non-toxic pharmaceutically acceptable adjuvant. Such adjuvants include but are not limited to oil emulsion and aluminum hydroxide ($AlOH_3$). Oil emulsion is the preferred adjuvant. More specifically, the killed EMCV vaccine comprises one or more isolates of an inactivated EMCV having pre-inactivation titers of $5 \times 10^6 - 1 \times 10^9 TCID_{50}$/dose, adjuvant and phosphate buffered saline (PBS). 30 μg/ml Gentamicin and 0.15-2% Formalin are added as preservatives.

The method of propagating the EMCV in a cell culture include the steps of inoculating the cells with EMC-25, incubating the cells until cytopathic effect (CPE) is noted, freeze-thawing the virus harvest and collecting the propagated virus from the harvest cells. Such cell cultures include but are not limited to baby hamster kidney-21 cells (BHK-21) and swine testicle cells (ST).

The vaccine is administered parenterally to sows or gilts several weeks before breeding a farrowing and to boars and growing piglets. The vaccine dosage can range up to 2 cc. If the vaccine is combined with other antigens, then it may be necessary to increase the dosage. The master seed and production seed are identified by characteristic cytopathic effect (CPE) in Baby Hamster Kidney-21 (BHK-21) cell cultures, fluorescent antibody or other serological tests. The production seed virus ranges between the master seed and the fourth BHK-21 cell culture passage. The vaccine virus ranges between the second and fifth BHK-21 cell culture passages. Seed stocks should be maintained in a frozen state at a temperature of not less than or equal to −40° C. or as lyophilized stock at not less than or equal to 7° C.

The seed and vaccine virus are propagated in BHK-21 cell cultures that have been tested in accordance with 9 CFR 113.52 and have been supplemented with cell culture medium. BHK-21 cells are suspended in growth medium at a rate of approximately $11 \times 10^5$ cells per ml. The cells are planted in sterile bottles at a rate of not less than $5 \times 10^4$ cells per cm$^2$ and are allowed to propagate until approximately 90% to 100% of the surface area is covered. These cells may be used for the propagation of EMCV or the cells may be expanded by passage to other bottles.

BHK-21 cell passages used for virus propagation range between Master Cell Stock (MCS) and MCS+25. This passaging is performed by discarding the growth medium, by adding sufficient quantities of a Trypsin Ethylenediaminetetraacetic Acid Solution (EDTA) to cover the surface of the bottle and by detaching the cells by shaking. The cell suspensions are resuspended in growth medium to equal not less than $5\times10^4$ cells per $cm^2$ of surface area of the bottle. All bottles are incubated at 37° C.±2° C. for 2-7 days. These cells may be re-fed with fresh medium if required.

Seed stocks are diluted in maintenance medium to provide $10^5$–$10^8$$TCID_{50}$/ml or are freshly passed one time in BHK-21 cells and added at the rate of one half to 10 ml of virus suspension per 100 ml. Cell cultures are inoculated when cell growth covers approximately 90%–100% of the surface area of the culture flask. The seed virus and maintenance medium suspension is inoculated onto the BHK-21 cell culture at the rate of 100 to 150 ml per 850 $cm^2$ bottles (Volume depends on cell conditions).

The EMCV infected monolayers are incubated at 37° C.±2° C. until CPE is evident, approximately 20-36 hours. CPE should be evident in 70–100% of the cells before harvest. Any container that has bacterial contamination, atypical monolayers, or does not show characteristic CPE is discarded.

Harvesting is normally done approximately 24 hours past inoculation. The minimum period of time that should elapse between the time of inoculation to harvest is 16 hours. The maximum amount of time is 72 hours. The bottles containing maintenance medium and infected cells are vigorously shaken to remove any remaining cells from the surface of the culture vessel. The cell suspension is pooled into liter bottles, approximately 1-15 liters per bottle.

As seen in Example 1, the virus harvest is inactivated. Adjuvant is added, at ambient temperatures, to the viral suspension to a final product concentration of approximately 20%. Sterile physiological saline containing 20 mg/L of phenol red, may be added to the inactivated virus and adjuvant suspension, depending on the virus titer, so that the final product composition will have no less than $10^{6.7}$$TCID_{50}$'s per dose or sufficient count to pass the potency test outlined in Example 2. Formaldehyde solution (37% Reagent Grade) is added at a concentration of no more than 0.2% v/v of the final volume of the product. Gentamicin is added at the time of serial assembly to a concentration not to exceed 30 μg/ml in the final product. The pH of the completed product is adjusted to 7.1±0.3 by the addition of sterile NaOH or HCl.

The product is standardized in the following way. Samples are taken from the pool harvest material prior to inactivation. The virus content is assayed by preparing 10-fold serial dilutions of the virus in cell culture medium. The virus dilutions are incubated onto monolayers of BHK-21 cells in 96-well microtiter plates or they are inoculated simultaneously with the cells. Each well is inoculated with 0.1 ml using 5 wells per dilution. The inoculated plates are incubated at 37° C.±2° C. under 5% $CO_2$ atmosphere. Titrations are read at 2-3 days post inoculation. Wells showing CPE are counted as positive virus infection. 50% endpoints are calculated in accordance with the Spearman-Karber method and are reported as tissue culture infection $dose_{50}$'s $(TCID)_{50}$. Satisfactory harvest cell culture material must contain not less than $10^{7.8}$$TCID_{50}$'s per ml prior to inactivation.

Bulk product, adjuvant and preservative are assembled aseptically into a single container. The suspension is mechanically agitated for no less than 15 minutes to obtain a uniform mixture. One or more batches may be pooled together to provide an average serial size of 100 liters. Continually agitated vaccine is vialed through a closed system into final containers. Each dose contains no less than $10^{6.7}$$TCID_{50}$'s of virus and no more than $10^9$ TCID's of virus.

Final container samples of each serial are tested for purity in accordance with 9 CFR 113.26. Bulk or final container samples of each serial are tested for safety in accordance with 9 CFR 113.33(b). The intraperitoneal route is used. Bulk or final container samples are tested for residual-free formaldehyde content using the Basic Fuchsin Test and should not contain residual formaldehyde greater than 0.2%. The expiration date of the product is at least 12 months from the date of the initiation of a satisfactory potency test. Depending upon the adjuvant, the vaccine should not be used within 30–60 days before slaughter. In case of an anaphylactic reaction, epinephrine is administered. The vaccine should be stored at 2°–7° C. and the entire vaccine should be used when the vaccine container is first opened.

The present invention is seen more fully by the examples below.

EXAMPLE 1

In this Example, we set forth the formulation of an EMC vaccine.

Baby hamster kidney 21 (BHK-21) cells are grown to monolayers in roller bottles which are incubated at 37° C. MEM with 10% fetal calf serum is used as the culture medium. The media is poured off the cells and the cells are rinsed once with Puck's Saline A. Fresh medium, MEM without fetal calf serum, is added to the cells.

The cells are inoculated with EMC-25 virus. The passage level of the EMC-25 virus must be within 5 subpassages from the master seed virus passage. The inoculated flashes are incubated at 37°±2° C. until CPE is noted to be complete, usually 16–48 hours.

The flasks containing the virus harvest are frozen at −5°-15° C. and then thawed. Freeze-thawing helps to rupture the cells and releases the virus. The virus harvest is pooled from all the infected flasks of cells.

The harvest is thoroughly mixed and a sample is obtained to determine the virus titer. The virus titer is determined by an endpoint titration using the Spearman-Karber method of determining 50% endpoints. The titer is expressed as $TCID_{50}$ (Tissue Culture Infection $Doses_{50}$). A typical virus harvest has a titer of $2\times10^9$$TCID_{50}$/ml.

The virus harvest is inactivated with Binary Ethylene Imine (BEI). 0.1M 2-bromoethylamine hydrobromide is converted to BEI by mixing with 0.2 normal sodium hydroxide (NaOH) and incubating for one hour in a 37° C. water bath. After conversion to BEI, the pH is adjusted to 7.4–7.8 with concentrated hydrochloric acid (HCl).

Inactivation is done at 37° C. for 24–48 hours. Sterile 1M sodium thiosulfate ($Na_2S_2O_3$) is added to the inactivated viral fluids at the rate of 20 ml/liter of fluids. This results in a final $Na_2S_2O_3$ concentration of 0.02 Molar. The $Na_2S_2O_3$ neutralizes the BEI so that it is no longer toxic.

A 10 ml sample of inactivated viral fluids is inoculated onto freshly monolayered BHK-21 cells. The cells are incubated for 3–5 days at 37° C. If no cytopathic effect (CPE) develops, the viral fluids are considered to be completely inactivated.

Using the pre-inactivation titer of the virus harvest, the vaccine is formulated as follows:

$5\times10^6$–$1\times10^9$ $TCID_{50}$/dose EMC virus, adjuvant, 30 μg/ml Gentamicin, 0.15–0.20% of Formalin Phosphate Buffered Saline (PBS). The pH of the completed product is adjusted to $7.1\pm0.3$ by the addition of sterile NaOH or HCl.

EXAMPLE 2

In this Example, we set forth a potency test of an EMC vaccine.

The potency testing is accomplished with bulk or final container product. Ten 3–4 week old piglets are tested for susceptibility to EMCV by the serum-neutralization (SN) test. Five pigs are vaccinated IM with 2 ml of the serial on test. The other five pigs are unvaccinated controls. The vaccinates are revaccinated 18–24 days later.

The pigs are bled 14–24 days after the first vaccination and the serums are assayed. A second blood sample is tested 18–42 days post vaccination. If the potency test requirements for a satisfactory serial are met after a single vaccination, the test can be concluded at this point.

The serums are assayed for SN antibodies to EMCV in 96 well microtiter plates seeded with BHK-21 cells. The serum dilutions are reacted with 50–500 $TCID_{50}$/well of EMC-25 virus. Both pre- and post-vaccination serums from each pig are assayed at the same time.

For a valid assay, all pre-vaccination sera must have SN titers of $<8$. Post vaccination serums from the unvaccinated control pigs must not show evidence of seroconversion to EMCV. If the test for a valid assay is not met, the test must be redone using new pigs.

The GMT SN titers of vaccinated pigs must be $\geqq 14$ in the post vaccination serum. At least 80% of the pigs must have SN titers of $\geqq 8$. Should the criteria for passage not be met, the test may be rerun once using at least 10 vaccinated and 5 control pigs to rule out animal variation. If the test is not repeated, the serial is unsatisfactory.

EXAMPLE 3

In this Example, we set forth the evaluation of vaccine formulations of varying antigenic dose and/or adjuvant by determining the serologic responses to each of the vaccines used to vaccinate susceptible swine. Six formulations of inactivated EMCV vaccines were tested. All vaccines were made form the same lot of inactivated virus fluids.

The antigen dose ranged from $10^{7.1}TCID_{50}$ to $10^{8.0}TCID_{50}$/2 ml dose. $AL(OH)_3$ and Imugen were compared as adjuvants. Two vaccinations, three weeks apart were given intramuscularly (IM). The pigs were bled three weeks and six weeks after the second vaccination.

The optimum antigen dose was between $10^{7.4}$ to $10^{7.7}TCID_{50}$/dose. The mean titers for vaccines in this antigen dose range were 21–32. A more uniform and consistent response was seen with the $Al(OH)_3$ adjuvant. Titers generally increased from 3–6 weeks after the second vaccination. A uniform and consistent response with moderate serum neutralization (SN) titers was achieved with several vaccine formulations.

EXAMPLE 4

In this Example, we set forth the evaluation of the immunogenicity of several inactivated EMCV vaccines in pregnant sows.

All of the vaccines contained 20% Imugen as an adjuvant. Vaccines A and B contained $10^8TCID_{50}$/2 ml dose of EMCV. (Vaccines A and B were prepared at different times). Vaccine C contained $10^{8.0}TCID_{50}$/2 ml dose of EMCV, Porcine Parvovirus, and three serovars of Leptospira species. For each vaccine, a sow was vaccinated IM at 6 and 2 weeks before farrowing.

After farrowing and ingestion of colostrum, 3-day old piglets were challenged with virulent EMCV. The sow that received vaccine A did not develop SN antibodies to EMC virus, and all of her piglets died within 5 days post challenge. The sows receiving vaccines B and C had post vaccination SN titers of 16. All of the piglets from these litters survived and none of the piglets had signs of clinical disease. Very mild histological changes were observed only after some of these piglets were sacrificed and necropsied at 6 or 9 days post-challenge.

Protection was clearly correlated with antibody titer of the vaccinated sows. No interference was seen in the combination vaccine compared to the monovalent EMC vaccine.

EXAMPLE 5

This Example illustrates the efficacy of an EMC vaccine in swine.

An inactivated Encephalomyocarditis virus (EMCV) vaccine was administered IM to 5 susceptible 3–4 week old weaned pigs. Five unvaccinated pigs were housed with the vaccinated pigs as controls. Serum neutralization (SN) antibody titers were measured in all 5 vaccinates (GMT-57) 20 days post vaccination, while SN titers remained negative in the controls. Twenty-four days post vaccination, vaccinates and controls were challenged with $10^{8.0}TCID_{50}$ of virulent EMCV (strain EMC-25) given IM in the ham. 100% of the controls had clinical signs of EMC 4–10 days post challenge, and 3 out of 5 (60%) of the controls died. None of the vaccinates died or had any clinical signs of disease during the study. The dead pigs had gross and histopathologic lesions characteristic of EMC, and EMC virus was isolated from heart and/or lung tissues of 2 of the 3 pigs that died. The third pig had an SN titer $\geqq 64$ on the day of death. The surviving controls had high SN titers to EMCV two weeks post challenge.

The results clearly demonstrate that the vaccine induced high levels of SN antibodies after a single vaccination in all vaccinates. The results further demonstrate that these antibody titers were highly protective against a severe challenge with virulent EMC which caused 100% morbidity and 60% mortality in unvaccinated control pigs.

We claim:

1. A vaccine which protects swine from clinical disease caused by encephalomyocarditis virus comprising inactivated encephalomyocarditis virus-25, adjuvant and a veterinary pharmaceutically acceptable carrier.

2. A vaccine according to claim 1 wherein the adjuvant is selected from the group consisting of oil emulsion and aluminum hydroxide.

3. A vaccine according to claim 1 wherein the inactivated encephalomyocarditis virus-25, has a pre-inactivation titer of $5 \times 10^6 - 1 \times 10^9 \, TCID_{50}/dose$.

4. A method of protecting swine against virulent encephalomyocarditis virus which comprises intramuscularly inoculating the swine with an inactivated encephalomyocarditis virus vaccine according to claim 1.

* * * * *